United States Patent
Inoue et al.

(10) Patent No.: US 9,060,701 B2
(45) Date of Patent: Jun. 23, 2015

(54) MEDICAL DIAGNOSTIC IMAGING APPARATUS

(75) Inventors: Yoshihiro Inoue, Kyoto (JP); Masaharu Amano, Kyoto (JP); Kazumi Tanaka, Kyoto (JP); Tetsuro Mizuta, Kyoto (JP); Atsushi Ohtani, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 389 days.

(21) Appl. No.: 13/147,419

(22) PCT Filed: Feb. 3, 2009

(86) PCT No.: PCT/JP2009/051745
§ 371 (c)(1),
(2), (4) Date: Aug. 2, 2011

(87) PCT Pub. No.: WO2010/089842
PCT Pub. Date: Aug. 12, 2010

(65) Prior Publication Data
US 2011/0288397 A1    Nov. 24, 2011

(51) Int. Cl.
*A61B 6/00* (2006.01)
*A61B 6/04* (2006.01)
*A61B 6/03* (2006.01)

(52) U.S. Cl.
CPC ............ *A61B 6/0457* (2013.01); *A61B 6/037* (2013.01); *A61B 6/4417* (2013.01); *A61B 6/5235* (2013.01)

(58) Field of Classification Search
CPC ...... A61B 6/037; A61B 6/032; A61B 6/4258; A61B 6/4417; A61B 6/5235; A61B 6/03
USPC .......................................... 600/407, 425, 436
See application file for complete search history.

(56) References Cited

U.S. PATENT DOCUMENTS

| 2007/0055127 A1* | 3/2007 | Ladebeck et al. ............. 600/407 |
| 2007/0129627 A1* | 6/2007 | Profio et al. .................. 600/407 |
| 2008/0008366 A1* | 1/2008 | Desh et al. .................... 382/128 |

FOREIGN PATENT DOCUMENTS

| JP | 59-153188 A | 9/1984 |
| JP | 2-167488 A  | 6/1990 |

(Continued)

OTHER PUBLICATIONS

Japanese Office Action with English Translation issued in Japanese Application No. 2010-549285 mailed Jan. 22, 2013.

(Continued)

*Primary Examiner* — Mark Remaly
(74) *Attorney, Agent, or Firm* — McDermott Will & Emery LLP (57) ABSTRACT

Provided is a medical image diagnosis apparatus which requires a small area for installation, has a short length in an axial direction of the apparatus, can reduce a problem of the strength of a top plate, and can simultaneously carry out dynamic PET-imaging of the entire body. A top plate (61) on which an examinee lies is moved through a tunnel of a CT gantry (2) and a PET gantry (3) to execute CT imaging and PET imaging. A PET unit consisting of a plurality (e.g. seven) of PET units (32) has a length of 2 m in the axis direction, the visual field thereof covers the whole body and the whole body can be simultaneously subjected to dynamic PET-imaging. For the maintenance of the PET gantry (3), the diagnosis apparatus is separated at an arbitrary PET unit (32) to be maintained, the apparatus slides on a rail (31) in the axis direction and is separated for maintenance operation. Accordingly, a large space for maintenance is not required and the area for installation is small.

6 Claims, 5 Drawing Sheets

(56) References Cited

FOREIGN PATENT DOCUMENTS

| JP | 4-268484 A | 9/1992 |
| JP | 9-211130 A | 8/1997 |
| JP | 2006-166968 A | 6/2006 |
| JP | 2008-134205 A | 6/2008 |

OTHER PUBLICATIONS

Japanese and English Translation of Chinese Office Action issued in Chinese Application No. 200980156144.3 mailed Oct. 8, 2012.

* cited by examiner

MEDICAL DIAGNOSTIC IMAGING APPARATUS

CROSS REFERENCE TO PRIOR APPLICATIONS

This application is a U.S. National Phase application under 35 U.S.C. §371 of International Application No. PCT/JP2009/051745, filed on Feb. 3, 2009. The International Application was published in Japanese on Aug. 12, 2010 as WO 2010/089842 A1 under PCT Article 21(2). All of the applications are herein incorporated by reference.

FIELD OF TECHNOLOGY

The present invention relates to a medical diagnostic imaging apparatus that is well-suited to early detection of cancer and microdose testing for pharmaceuticals, and, in particular, relates to a medical diagnostic imaging apparatus that combines a wide-field full-body PET (Positron Emission Computer Tomography) apparatus and an x-ray CT apparatus (a CT scanner).

PRIOR ART

In a PET apparatus, a drug that has the characteristic of accumulating in cancers and tumors is marked with a nuclide that emits positrons, and that drug is injected into the human body. The location and intensity of the emission of gamma rays that are emitted when positrons are annihilated are captured by a detecting device to collect data, which is subjected to processing to reconstruct an image of the distribution of the nuclides. The image distributions show concentration distributions of the nuclides in cross-sectional slices of the human body in the planes in which the detecting devices are arrayed.

In the x-ray CT apparatus, an x-ray CT image is produced through scanning the body of a patient with an x-ray in slices that are perpendicular to the anteroposterior axis. The x-ray CT image shows the state of the tissue within the human body in those slices. Given this, in order to produce a reliable diagnosis, the PET imaging, which shows the concentration distribution of the nuclides in the slices, and the x-ray CT imaging, which shows the state of the tissue within the body in the slices, are used together to perform the diagnosis. Here it is necessary for the slices in the PET image and in the x-ray CT image to match each other precisely.

Given this, medical diagnostic imaging apparatuses have been proposed that solve the problem of misalignment of the slice images due to deflection of the table, which is cantilevered from one end, when the table on which the patient lies is inserted into the gantry tunnel portion of the PET apparatus and inserted into the gantry tunnel portion of the x-ray CT apparatus. (See Patent Reference 1, for example.)

On the other hand, the field of view in the direction of the anteroposterior axis of a typical PET apparatus is between about 15 cm and 25 cm, making it impossible to perform PET imaging on the entire body all at once. When performing PET imaging of the entire body, an extensive period of time is required in order to move the table on which the patient lies.

In recent years there has been considerable interest in microdose testing. This is testing that is performed in order to do screening for optimal compounds from among new candidate drug compounds through single injections of extremely small doses of the compounds into humans, where it is necessary to obtain a distribution image of the candidate drug compound in the human body dynamically. In a PET apparatus, it is possible to mark the compound with a positron nuclide to be able to measure sequentially the distribution images of the compound not only in the blood and the urine, but also in the organs and tissue, through joint use with an x-ray CT image that shows the state of the tissue within the human body through an x-ray CT apparatus.

However, in microdose testing, there is the need to be able to perform dynamic PET imaging of the entire body all at once (where changes over time in the drug distribution are imaged by reconstructing images of the various data through performing PET imaging of the same location with a set time of, for example, once per minute). While it is not possible to perform imaging of the entire body with a PET apparatus having a field of view in the direction of the anteroposterior axis of between about 15 cm and 25 cm, dynamic PET imaging is performed for, for example, that head.

Figure 4:
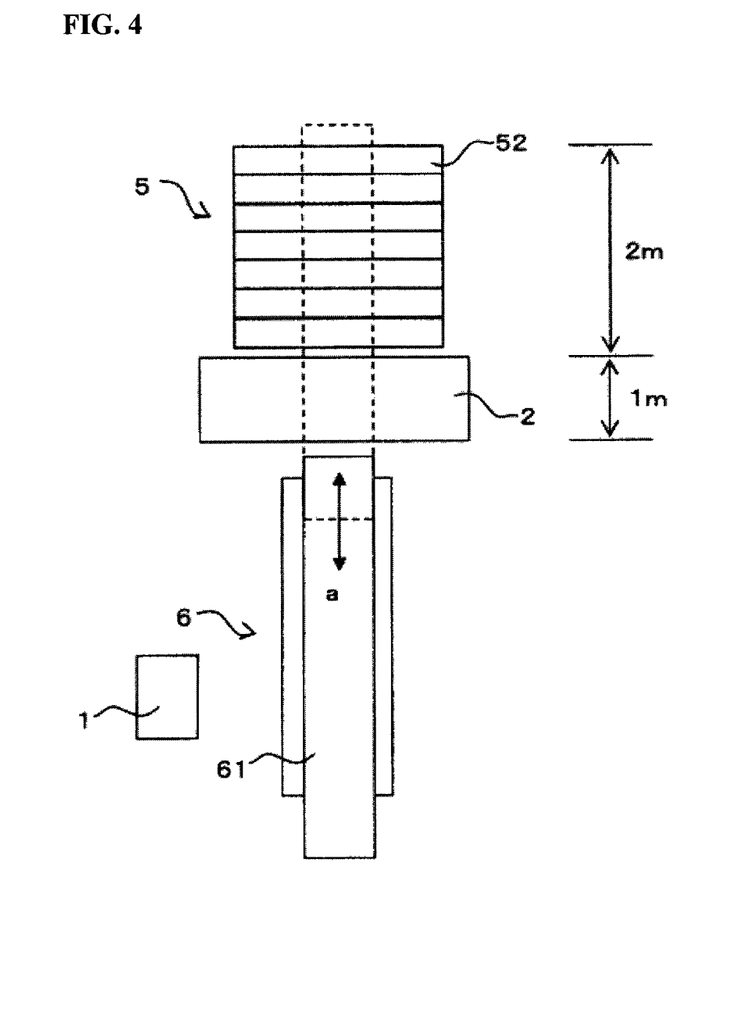
FIG. 4 is a diagram illustrating a schematic structure of a conventional medical diagnostic imaging apparatus.

FIG. 4 is a diagram illustrating schematically a medical diagnostic imaging apparatus that combines a PET apparatus and an x-ray CT apparatus in a conventional layout. The medical diagnostic imaging apparatus, as illustrated in FIG. 4, is structured from: a PET gantry 5 that is structured from a plurality of PET units 52 that are segmented in the direction of the anteroposterior axis; a CT gantry that is disposed in a straight line with the PET gantry in the direction of the anteroposterior axis 5; a bed 6 that is provided with a table 61 that can slide in the direction a of the anteroposterior axis to enter into the PET gantry 5 and the CT gantry 2; and a console 1 for performing equipment control and image data processing; where innovations have been performed so that the field of view in the PET gantry 5 is able to cover the entire body, so as to enable dynamic PET imaging of the entire body all at once.

The table 61 on which the patient lies enters into the tunnels for the CT gantry 2 and the PET gantry 5 to perform CT imaging and PET imaging. The PET gantry 5 that is structured from a plurality (for example, 7) of PET units 52 has a length of approximately 2 m in the direction of the anteroposterior axis, where the length of the CT gantry 2 in the direction of the anteroposterior axis is approximately 1 m, so that the length of the gantry as a whole is approximately 3 m.

Figure 5:
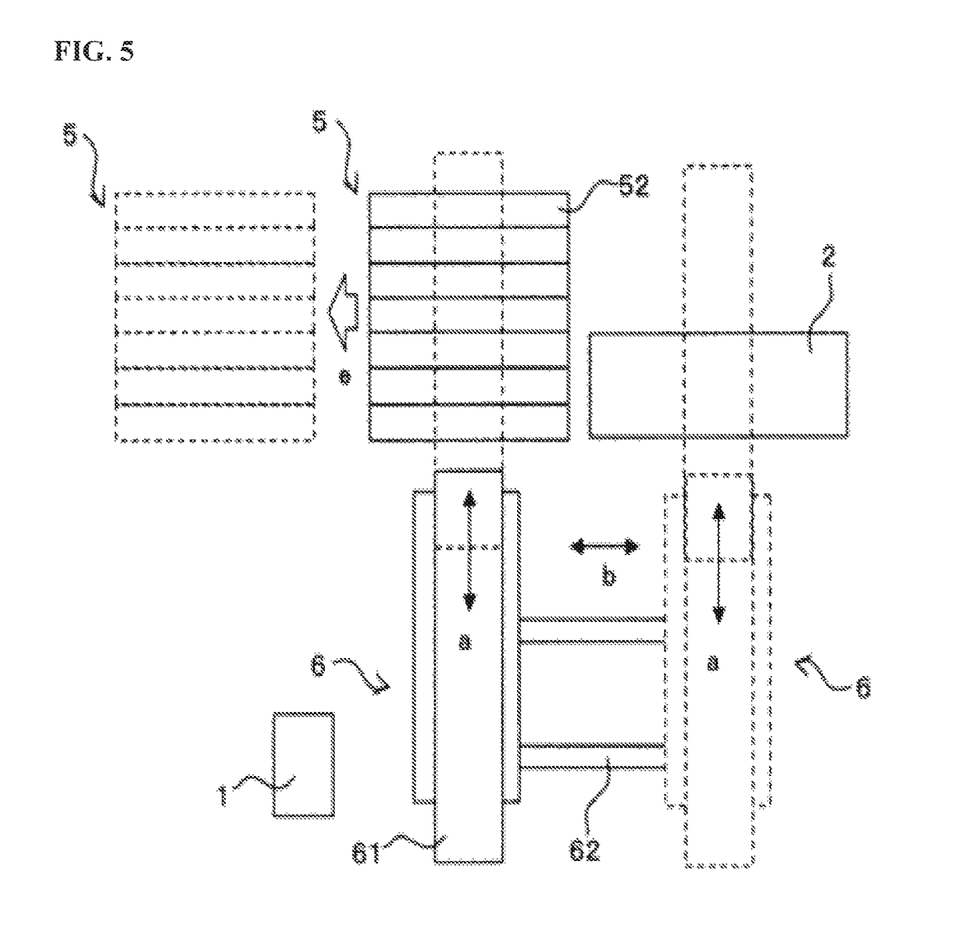
FIG. 5 is a diagram illustrating a schematic structure of a conventional medical diagnostic imaging apparatus.

On the other hand, a medical diagnostic imaging apparatus has been proposed that combines together a PET apparatus able to perform dynamic PET imaging of the entire body all at once and an x-ray CT apparatus in a side-by-side arrangement. This medical diagnostic imaging apparatus, as illustrated in FIG. 5, is structured from: a PET gantry 5 that is structured from a plurality of PET units 52 that are segmented in the direction of the anteroposterior axis; a CT gantry 2 that is arranged beside the PET gantry 5; a bed 6 that is provided with a table 61 that can slide in the direction a of the anteroposterior axis to enter into the PET gantry 5 or the CT gantry 2; and a console 1 for performing equipment control and image data processing. The bed 6, when in a state wherein the table 61 has been withdrawn from the tunnel, shifts in a direction b that is perpendicular to the anteroposterior axis on rails 62, to stop in front of the tunnel for the PET gantry 5 or the CT gantry 2.

The table 61 on which the patient lies sequentially enters into the tunnels for the CT gantry 2 and the PET gantry 5 to perform CT imaging and PET imaging. The PET gantry 5 that is structured from a plurality of PET units 52 has a length of approximately 2 m in the direction of the anteroposterior axis, and has a field of view that can cover the entire body, enabling dynamic PET imaging of the entire body all at once. At the time of maintenance, each PET unit 52 slides in the direction e that is perpendicular to the anteroposterior axis, to be split, to enable maintenance.

Patent Reference 1: Japanese Unexamined Patent Application Publication 2006-166968

DISCLOSURE OF THE INVENTION

Problem Solved by the Present Invention

The medical diagnostic imaging apparatus illustrated in FIG. 4 is able to perform dynamic PET imaging of the entire body all at once, and the total length of the CT gantry 2 and the PET gantry 5 in the direction of the anteroposterior axis is about 3 m, which is an extremely long equipment configuration. Additionally, because it is necessary for the length of the table 61, upon which the patient lies and which enters into the gantry tunnel, to be at least 3 m, the strength of the table 61 becomes problematic.

The medical diagnostic imaging apparatus illustrated in FIG. 5 is also able to perform dynamic PET imaging of the entire body all at once, and requires the space illustrated by the dotted line (the same space as the PET gantry 5) when maintenance is performed on the PET gantry 5, increasing the area required by the apparatus.

Means for Solving the Problem

The present invention is a medical diagnostic imaging apparatus that is provided with an x-ray CT apparatus and a PET apparatus that are provided with a gantry that is structured from a line of a plurality of PET units that are supported so as to enable splitting in the direction of the anteroposterior axis, comprising: splitting/moving means for splitting line of PET units at an arbitrary PET unit and moving in the direction of the anteroposterior axis. Moreover, the tunnels for the PET apparatus and the x-ray CT apparatus are arranged side-by-side. Consequently, maintenance can be performed in a small space, and the length of the table is short.

Effects of the Invention

The present invention enables maintenance operations in a small space, where the area required by the apparatus is reduced, and the length of the apparatus in the direction of the anteroposterior axis is also shortened, as is the length of the table, reducing the problems with the table strength. Furthermore, the present invention is able to provide a medical diagnostic imaging apparatus capable of dynamic PET imaging of the entire body all at once.

EXPLANATION OF CODES

1: Console
2: CT Gantry
3: PET Gantry
4: PET Gantry
5: PET Gantry
6: Bed
7: Bed
11: Input Device
12: Imaging Controlling Device
13: CT Image Reconstructing Device
14: PET Image Reconstructing Device
15: Image Fusing Device
16: Image Displaying Device
21: Rail
22: X-Ray Tube
23: X-Ray Generating Device
24: CT Detecting Device
25: Data Gathering Device
31: Rail
32: PET Unit
41: Rail
42: PET Unit
52: PET Unit
61: Table
62: Rail
63: Controlling Device
64: Driving Device
71: Stationary Table
72: Rail
321: PET Detecting Device
322: Data Gathering Device
a: Direction of Anteroposterior Axis
b: Direction Perpendicular to the Anteroposterior Axis
c: Direction Parallel to the Anteroposterior Axis
d: Direction Parallel to the Anteroposterior Axis
e: Direction Perpendicular to the Anteroposterior Axis Most Preferred Form For Carrying Out The Invention The number of the plurality of PET units that are supported so as to enable splitting in the direction of the anteroposterior axis, which structure the PET gantry, is, for example, about 7. The field of view in this configuration can cover the entire body.

Example of Embodiment 1

Figure 1:
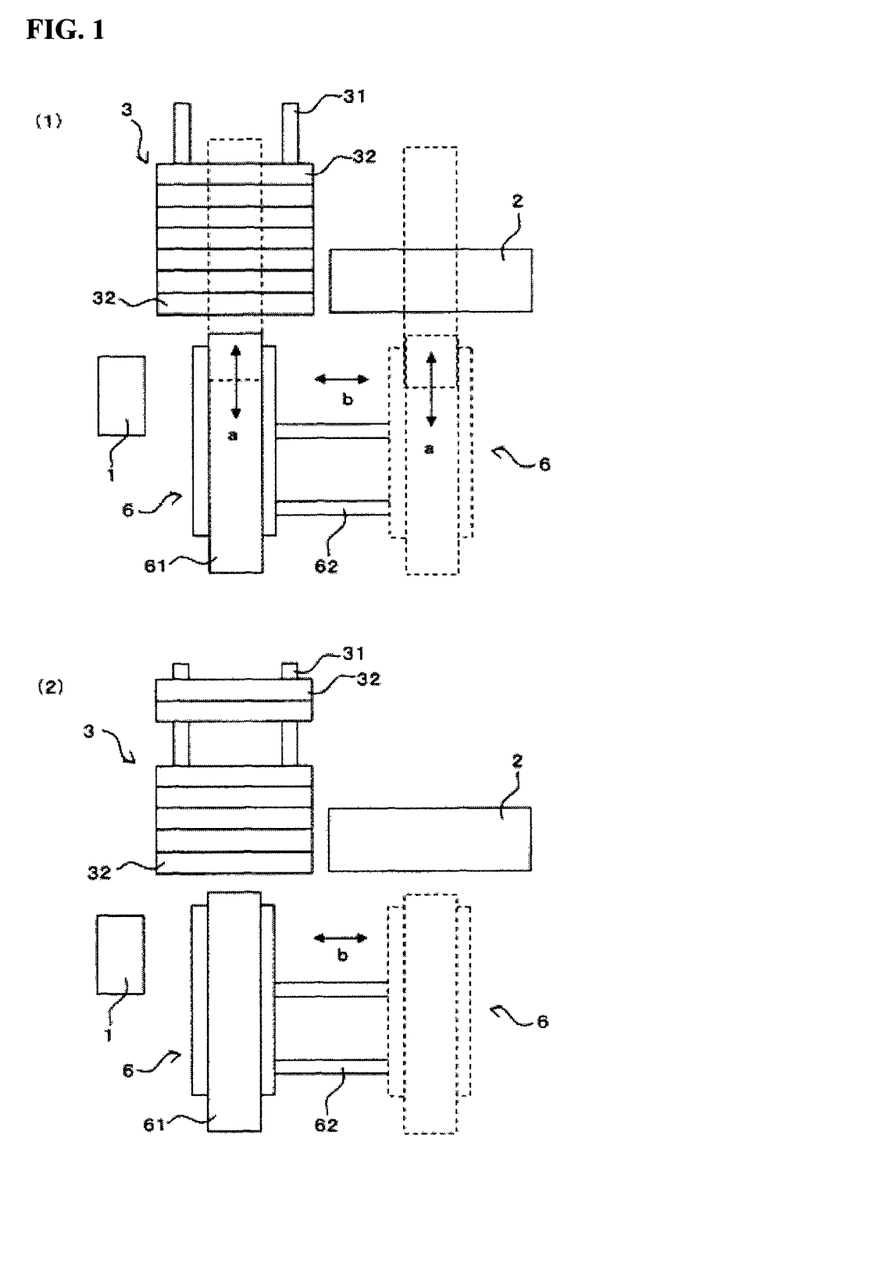
FIG. 1 is a diagram illustrating a schematic structure for a medical diagnostic imaging apparatus according to an example of embodiment according to the present invention.
Figure 2:
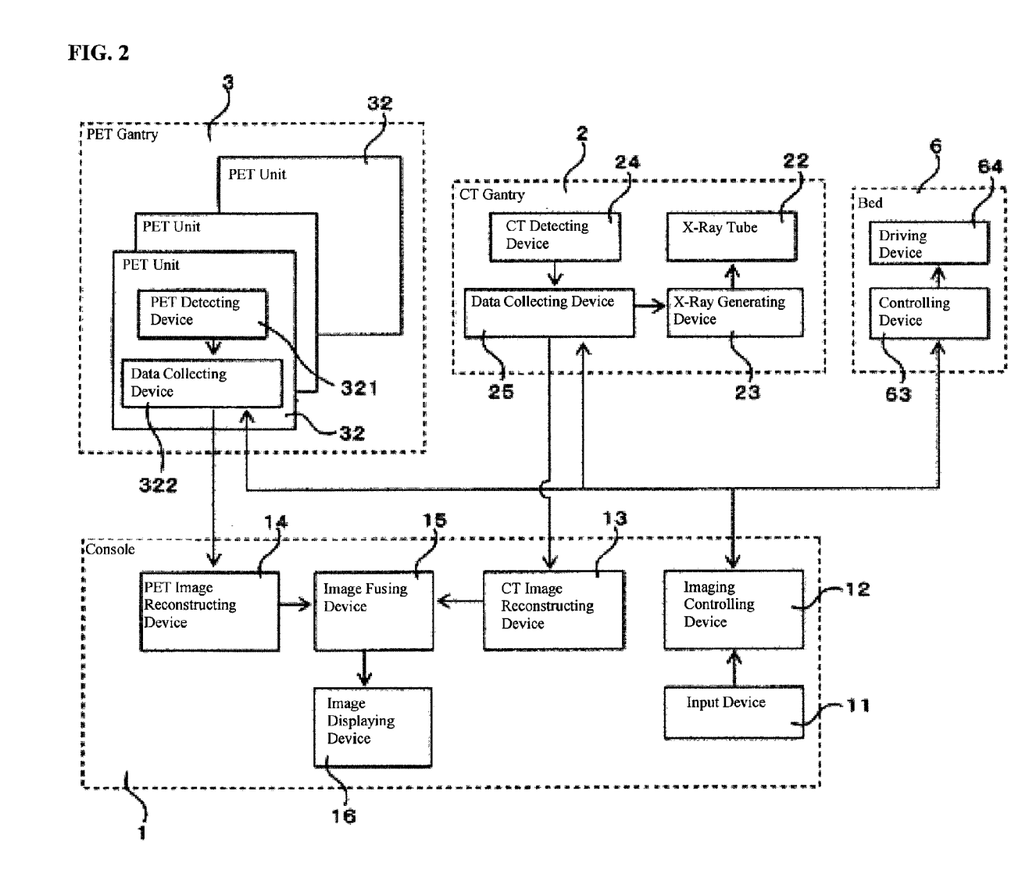
FIG. 2 is a block diagram illustrating schematically the operation of the medical diagnostic imaging apparatus according to the example of embodiment according to the present invention.

A first example of embodiment according to the present invention will be explained in reference to FIG. 1 and FIG. 2. FIG. 1 is a diagram illustrating a schematic structure for a medical diagnostic imaging apparatus according to the first example of embodiment according to the present invention. FIG. 2 is a block diagram illustrating schematically the operation of the medical diagnostic imaging apparatus according to the first example of embodiment according to the present invention.

The medical diagnostic imaging apparatus according to the first example of embodiment according to the present invention, as illustrated in FIG. 1 (1) is structured from: a PET gantry 3 that is structured from a plurality of PET units 32, on rails 31, segmented so as to enable splitting in the direction of the anteroposterior axis; a CT gantry 2 that is disposed beside the PET gantry 3; a bed 6 that supports a table 61 so as to be able to slide in the direction a of the anteroposterior axis so as to be able to enter into the tunnel of the PET gantry 3 or of the CT gantry 2; and a console 1 for performing equipment control and image data processing. The bed 6 moves in the direction b that is perpendicular to the anteroposterior axis on rails 62 in a state wherein the table 61 is withdrawn from the tunnel, and stops in front of the tunnel for the PET gantry 3 or for the CT gantry 2.

The table 61 upon which the patient lies enters sequentially into the tunnels of the CT gantry 2 that structures the x-ray CT apparatus and of the PET gantry 3 that structures the PET apparatus, to perform CT imaging and PET imaging. The PET gantry 3 that is structured from a plurality (for example, 7) of PET units 32 has a length of about 2 m in the direction of the anteroposterior axis, and has a field of view that covers the entire body, so is able to perform dynamic PET imaging of the entire body all at once.

At the time of maintenance on the PET gantry 3, a split is made at any given PET unit 32 requiring maintenance, to slide in the direction of the anteroposterior axis on the rail 31, to split in order to perform the operation, as illustrated in FIG. 1 (2). Note that the components in FIG. 1 (2) indicated by the same codes as in FIG. 1 (1) are identical to those in FIG. 1 (1), so explanations thereof are omitted.

First, the operation of the medical diagnostic imaging apparatus according to the first form of embodiment according to the present invention will be explained in reference to FIG. 2. Imaging conditions for the PET imaging and CT imaging are inputted into an imaging controlling device 12 through an input device 11 provided at a console 1. The patient that has been injected with the radioactive medicine lays on the table 61 (FIG. 1) of the bed 6, and is placed in the tunnel of the CT gantry 2. The image controlling device outputs commands to the data-gathering device 25 of the CT gantry 2 and to the controlling device 63 of the bed 6 based on the imaging conditions for CT imaging inputted by the image controlling device 12. The x-ray tube 22 is exposed to x-rays by the x-ray generating device 23 while rotating, and the table 61 (FIG. 1) is moved by a driving device 64, and the x-rays that pass through the body are detected by the CT detecting device 24 to perform the CT imaging. The CT data obtained are sent to the CT image reconstructing device 13 of the console 1 to reconstruct the CT image.

Second, the bed 6 slides in the direction b (FIG. 1) that is perpendicular to the anteroposterior axis, to move in front of the PET gantry 3, and the patient enters into the tunnel of the PET gantry 3. The imaging controlling device 12 outputs commands to the data gathering devices 322 of the plurality (for example, 7) of PET units 32 that structure the PET gantry 3, based on the inputted imaging conditions for the PET imaging, to perform PET imaging by detecting, by the PET detecting device 321, the gamma rays emitted from the radioactive drug. The PET data obtained are sent to the PET image reconstructing device 14 in the console 1, to reconstruct the PET image. The CT image and the PET image are sent to the image fusing device 15, where the two images are superimposed and displayed on an image displaying device 16.

Example of Embodiment 2

Figure 3:
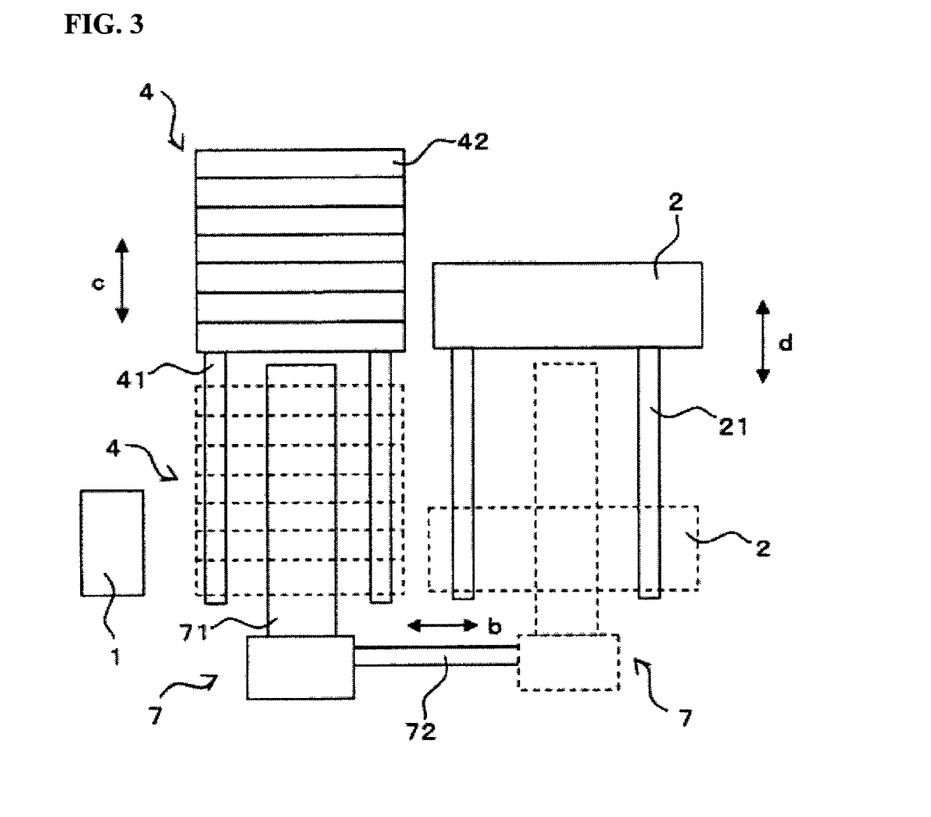
FIG. 3 is a schematic structural diagram of a modified example of the present invention.

A second example of embodiment according to the present invention will be explained in reference to FIG. 3. The medical diagnostic imaging apparatus according to the second example of embodiment according to the present invention, as illustrated in FIG. 3, is structured from: a PET gantry 4 that is supported so as to be able to slide on a rail 41 in the direction of direction c that is parallel to the anteroposterior axis, and is structured from a plurality (for example, 7) of PET units 42 that are segmented so as to enable splitting in the direction of the anteroposterior axis; a CT gantry 2 that is arranged beside the PET gantry 4, held so as to be able to slide on a rail 21 in the direction d that is parallel to the anteroposterior axis; a bed 7, provided with a stationary table 71, provided so as to be able to slide on a rail 72 in the direction b that is perpendicular to the anteroposterior axis; and a console 1 for device control and image data processing. The bed 7 moves in the direction b that is perpendicular to the anteroposterior axis on a rail 72 when the positions of the PET gantry 4 and the CT gantry 2 are in the state shown by the solid line, to stop in front of the tunnel of the PET gantry 4 or of the CT gantry 2.

The patient lies on the stationary table 71, and CT imaging is performed when the CT gantry 2 that structures the x-ray CT apparatus and the bed 7 are at the positions of the dotted lines, and PET imaging is performed when the PET gantry 4 that structures the PET apparatus is at the position of the dotted lines and the bed 7 is at the position of the solid lines.

The PET gantry 4 that is structured from a plurality (for example, 7) of PET units 42 has a length of about 2 m in the direction of the anteroposterior axis, where the field of view covers the entire body, enabling dynamic PET imaging of the entire body all at once. At the time of maintenance on the PET gantry 4, a split is made at any given PET unit 42 requiring maintenance, to slide in the direction of the anteroposterior axis on the rail 41, to split in order to perform the operation.

Because the present invention is structured as set forth above, the maintenance operation can be done in a small space when compared to the medical diagnostic imaging apparatus illustrated in FIG. 5, reducing the space required for installation. Moreover, when compared to the medical diagnostic imaging apparatus illustrated in FIG. 4, not only is the length of the apparatus in the direction of the anteroposterior axis reduced, but also the lengths of the table 61 and the stationary table 71 are reduced as well, reducing the problem with strength. Moreover, this can provide a medical diagnostic imaging apparatus able to perform dynamic PET imaging of the entire body all at once.

In the first example of embodiment, illustrated in FIG. 1, the line of the plurality of PET units 32 is split at an arbitrary PET unit 32 requiring maintenance, so slide on the rail 31 in the direction away from the bed 6, but, conversely, the opposite side of the split may be slid in the direction of the bed 6. The modified example set forth above can be embodied in the second example of embodiment illustrated in FIG. 3. Note that in the first example of embodiment, illustrated in FIG. 1, even if the PET unit 32 that is disposed at the very end of the line is stationary, the present invention can still be applied. The present invention is not limited to the illustrated examples set forth above, but rather includes a variety of modified examples as well.

APPLICABILITY IN INDUSTRY

The present invention relates to a medical diagnostic imaging apparatus that is well-suited to the early detection of cancer and microdose testing regarding pharmaceuticals, and, in particular, can be used in a medical diagnostic imaging apparatus that combines a large-field PET apparatus and an x-ray CT.

The invention claimed is:

1. A medical diagnostic imaging apparatus comprising:
a Positron Emission Computer Tomography (PET) apparatus including a first gantry, the first gantry having a first tunnel into which a patient is inserted; and
an x-ray Computed Tomography (CT) apparatus including a second gantry having a second tunnel into which the patient is inserted, wherein
the first gantry is dividable into PET units along a first direction of inserting the patient into, or a second direction of removing the patient from, the first tunnel of the first gantry, each PET unit comprising a PET detector configured to detect a gamma ray, each PET unit being configured to be movable in the first and second directions,
the PET apparatus further comprises a guide configured to move each PET unit in the first and second directions, and
the PET apparatus has an operation mode and a maintenance mode, in the operation mode, the PET units are connected together to allow the patient to be inserted into the first gantry for obtaining a PET image, and in the maintenance mode, at least one PET unit is separated from others along the guide to perform maintenance of the PET apparatus.

2. The medical diagnostic imaging apparatus as set forth in claim 1, wherein the first tunnel for the PET apparatus and the second tunnel for the x-ray CT apparatus are disposed next to each other.

3. The medical diagnostic imaging apparatus as set forth in claim 1, wherein the first and second gantries are arranged so that the first and second tunnels are parallel with each other.

4. The medical diagnostic image apparatus as set forth in claim 1, wherein two or more of the PET units separated from other PET units are movable together in the first and second directions.

5. The medical diagnostic image apparatus as set forth in claim 4, wherein the two or more of the PET units is separated from the other PET units at a location between one PET unit and another PET unit next to the one PET unit.

6. The medical diagnostic image apparatus as set forth in claim 1, wherein the guide includes rails for supporting each PET units.

\* \* \* \* \*